United States Patent
Hatakeyama

(10) Patent No.: US 9,585,720 B2
(45) Date of Patent: Mar. 7, 2017

(54) MEDICAL MANIPULATOR AND TREATMENT TOOL REPLACEMENT METHOD

(71) Applicant: OLYMPUS CORPORATION, Tokyo (JP)

(72) Inventor: Naoya Hatakeyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 14/562,898

(22) Filed: Dec. 8, 2014

(65) Prior Publication Data

US 2015/0094737 A1 Apr. 2, 2015

Related U.S. Application Data

(63) Continuation of application No. PCT/JP2013/069654, filed on Jul. 19, 2013.

(30) Foreign Application Priority Data

Jul. 31, 2012 (JP) .................................. 2012-169666

(51) Int. Cl.
A61B 19/00 (2006.01)

(52) U.S. Cl.
CPC .......... *A61B 19/2203* (2013.01); *A61B 34/30* (2016.02); *A61B 34/37* (2016.02);
(Continued)

(58) Field of Classification Search
CPC ...... A61B 19/2203; A61B 2017/00477; A61B 2017/715; A61B 2034/306; A61B 34/30; A61B 34/37; A61B 34/77; Y10T 29/4973
(Continued)

(56) References Cited

U.S. PATENT DOCUMENTS 6,752,037 B1 *  6/2004  Miyazawa .......... B23B 31/1078
                                                       403/322.1
7,720,322 B2     5/2010  Prisco
(Continued)

FOREIGN PATENT DOCUMENTS

JP       04-263831 A      9/1992
JP     2004-105451 A      4/2004
(Continued)

OTHER PUBLICATIONS

International Search Report dated Aug. 20, 2013 issued in PCT/JP2013/069654.
(Continued)

*Primary Examiner* — Khoi Tran
*Assistant Examiner* — Robert Nguyen
(74) *Attorney, Agent, or Firm* — Scully, Scott, Murphy & Presser, PC

(57) ABSTRACT

A medical manipulator includes: an operation member configured to drive so as to operate a treatment tool; a treatment tool side drive shaft configured to rotate about an axis thereof so as to drive the operation member; an operation amount detection member connected to the treatment tool; a treatment tool side detection shaft configured to rotate about an axis thereof in accordance with displacement of the operation amount detection member; a drive unit side drive shaft engaged with the treatment tool side drive shaft; a drive unit side detection shaft engaged with the treatment tool side detection shaft; a shape regulation section configured to regulate a shape of the treatment tool to a predetermined operation state; and a phase setting section configured to set phases in rotational directions of the treatment tool side drive shaft and the treatment tool side detection shaft.

9 Claims, 19 Drawing Sheets

(52) U.S. Cl.
CPC ........ *A61B 34/77* (2016.02); *A61B 2034/306* (2016.02); *Y10T 29/4973* (2015.01)

(58) Field of Classification Search
USPC ....................................... 606/130; 29/402.08
See application file for complete search history.

(56) References Cited

U.S. PATENT DOCUMENTS

| | | |
|---|---|---|
| 2004/0049205 A1 | 3/2004 | Lee et al. |
| 2008/0177403 A1* | 7/2008 | Masuya ............. G05B 19/4061 700/90 |
| 2008/0221592 A1* | 9/2008 | Kawai .................. A61B 1/0055 606/130 |
| 2010/0241135 A1 | 9/2010 | Iida |
| 2011/0282154 A1 | 11/2011 | Umemoto |
| 2012/0048628 A1* | 3/2012 | Kawanami ............. B25J 9/0003 180/21 |

FOREIGN PATENT DOCUMENTS

| | | |
|---|---|---|
| JP | 2008-104854 A | 5/2008 |
| JP | 2009-148859 A | 7/2009 |
| WO | WO 2010/126127 A1 | 11/2010 |

OTHER PUBLICATIONS

Extended Supplementary European Search Report dated Mar. 17, 2016 in related European Application No. 13 82 5932.0.

* cited by examiner

MEDICAL MANIPULATOR AND TREATMENT TOOL REPLACEMENT METHOD

This application is a continuation application based on a PCT Application No. PCT/JP2013/069654, filed Jul. 19, 2013, whose priority is claimed on Japanese Patent Application No. 2012-169666, filed Jul. 31, 2012. The contents of the both the PCT Application and the Japanese Application are incorporated herein by reference.

BACKGROUND OF THE INVENTION

Field of the Invention

The present invention relates to a medical manipulator and a treatment tool replacement method. More specifically, the present invention relates to a medical manipulator in which a plurality of replaceable treatment tools are mounted and used, and a treatment tool replacement method in the medical manipulator.

Description of Related Art

Conventionally, it is known that a medical manipulator includes various types of treatment tools detachably attached to a body thereof, and the treatment tools are properly selected according to a procedure to be performed, target tissue, etc. so as to be mounted to the body and used. For example, PCT International Publication No. WO 2010/126127 discloses a medical manipulator in which a body having a drive section and a work section equivalent to a treatment tool are detachably attached to each other.

Among treatment tools of a medical manipulator, there is a treatment tool in which a bending section is provided at a distal end side thereof and bent in a desired direction by operation of an operation member such as a wire using a drive section, so as to perform a procedure. Accordingly, in order to allow a curved state of the treatment tool to correspond to the operation of a practitioner with high accuracy, the drive section needs to engage with the treatment tool in a state in which their phases coincide. However, when the treatment tool is removed from a body for replacement, a shaft of the drive section or the like is in a free state due to the release of the engagement and may thus rotate due to self-weight or the like. When another treatment tool is mounted after occurrence of such rotation, the phases do not coincide. As a result, there is a problem in that correspondence accuracy between the state of the treatment tool and the operation of the practitioner deteriorates.

In consideration of the above problem, the medical manipulator of PCT International Publication No. WO 2010/126127 is configured such that a drive section side engagement section is provided with a detection pin advancing and retracting in an axial direction of a drive shaft and a work section side engagement section is provided with a cam surface having a height changed in an axial direction in a circumferential direction. The medical manipulator is provided with a sensor for detecting a position of the detection pin changed by abutting the cam surface, thereby allowing a phase of the work section side to be detected at the drive section side in an interconnected state.

Accordingly, even though the drive section is attached to the work section in a state in which their phases are deviated from each other when the work section is replaced or remounted, a phase difference between the drive section side and the work section side can be detected. Accordingly, angle correspondences (phases) between the drive section and the work section can be made to coincide by performing correction of the detected phase difference.

SUMMARY OF THE INVENTION

According to a first aspect of the present invention, a medical manipulator including a drive unit, and a treatment tool detachably mounted on the drive unit and configured to be driven by the drive unit, includes: an operation member connected to the treatment tool and configured to drive so as to operate the treatment tool; a treatment tool side drive shaft configured to rotate about an axis thereof so as to drive the operation member; an operation amount detection member connected to the treatment tool; a treatment tool side detection shaft configured to rotate about an axis thereof in accordance with displacement of the operation amount detection member; a drive unit side drive shaft having a drive section configured to generate a driving force, installed at the drive unit, and configured to be engaged with the treatment tool side drive shaft so as to transmit the driving force to the treatment tool side drive shaft; a drive unit side detection shaft having a detection section configured to detect a displacement amount of the operation amount detection member, installed at the drive unit, and configured to be engaged with the treatment tool side detection shaft such that rotation of the treatment tool side detection shaft is transmitted to the drive unit side detection shaft; a shape regulation section configured to regulate a shape of the treatment tool to a predetermined operation state in which the treatment tool is operated by a predetermined operation amount; and a phase setting section configured to set phases in rotational directions of the treatment tool side drive shaft and the treatment tool side detection shaft. The phase setting section sets the phases of the treatment tool side drive shaft and the treatment tool side detection shaft to correspond to the predetermined operation state when the phase setting section receives a predetermined signal.

According to a second aspect of the present invention, in the medical manipulator according to the first aspect of the present invention, the shape regulation section may have a detection unit configured to send a signal to the phase setting section when the treatment tool is regulated as the predetermined operation state, and the phase setting section may set the phases of the treatment tool side drive shaft and the treatment tool side detection shaft to correspond to the predetermined operation state when the phase setting section receives the signal from the detection unit.

According to a third aspect of the present invention, in the medical manipulator according to the first or second aspect of the present invention, the treatment tool may have a bending section, and the predetermined operation state may be a state in which the bending section is linear.

According to a fourth aspect of the present invention, in the medical manipulator according to the third aspect of the present invention, the treatment tool may further have an end effector installed at a tip of the bending section, and the shape regulation section may have a first region configured to regulate a shape of the bending section and a second region configured to regulate a shape of the end effector.

According to a fifth aspect of the present invention, in the medical manipulator according to the third aspect of the present invention, the shape regulation section may have a pressing member configured to press the bending section to become a linear shape.

According to a sixth aspect of the present invention, there is provided a treatment tool replacement method in a medical manipulator including: a drive unit; a treatment tool detachably mounted on the drive unit and configured to be driven by the drive unit; an operation member connected to the treatment tool and configured to drive so as to operate the treatment tool; a treatment tool side drive shaft configured to rotate about an axis thereof so as to drive the operation member; an operation amount detection member connected to the treatment tool; a treatment tool side detection shaft configured to rotate about an axis thereof in accordance with displacement of the operation amount detection member; a drive unit side drive shaft having a drive section configured to generate a driving force, installed at the drive unit, and configured to be engaged with the treatment tool side drive shaft so as to transmit the driving force to the treatment tool side drive shaft; and a drive unit side detection shaft having a detection section configured to detect a displacement amount of the operation amount detection member, installed at the drive unit, configured to be engaged with the treatment tool side detection shaft such that rotation of the treatment tool side detection shaft is transmitted to the drive unit side detection shaft. The treatment tool replacement method includes: mounting the treatment tool on the drive unit, and engaging the treatment tool side drive shaft with the drive unit side drive shaft and engaging the treatment tool side detection shaft with the drive unit side detection shaft; holding a shape of the treatment tool to a predetermined operation state in which the treatment tool is operated by a predetermined operation amount; and setting phases in rotational directions of the treatment tool side drive shaft and the treatment tool side detection shaft to correspond to the predetermined operation state.

DETAILED DESCRIPTION OF THE INVENTION

First Embodiment

Figure 1:
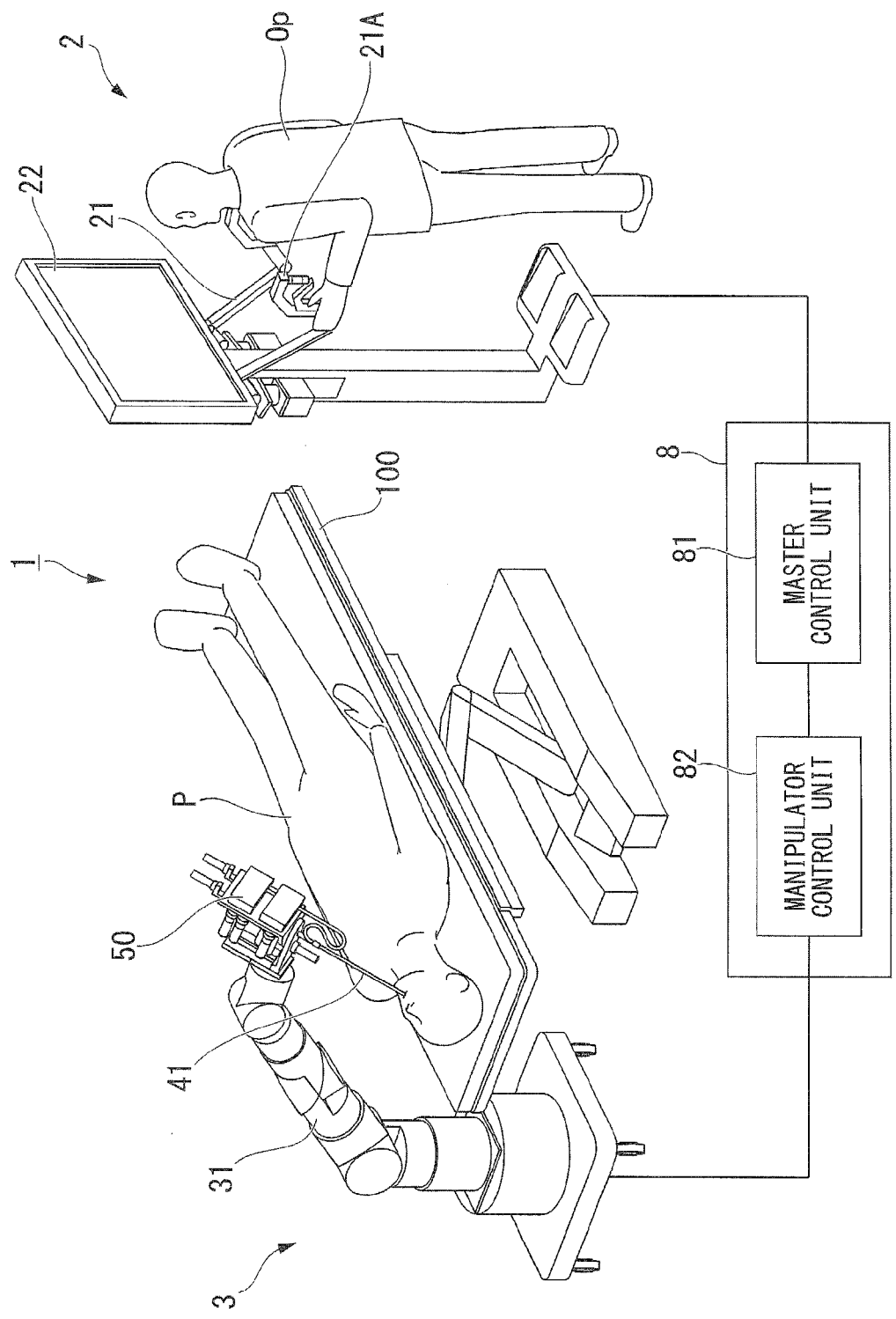
FIG. 1 is a view illustrating an entire configuration of a master-slave system which is a medical manipulator according to a first embodiment of the present invention.

Hereinafter, a first embodiment of the present invention will be described with reference to FIGS. 1 to 13. FIG. 1 is a view illustrating an entire configuration of a master-slave system 1 which is a medical manipulator of the present invention. The master-slave system 1 includes a master input section 2 which has a master arm 21 and issues an operation command, and a slave manipulator 3 having a slave arm 31. The master-slave system 1 remotely controls the slave arm 31 such that the slave arm 31 is tracked according to operation of the master arm 21 by a practitioner (operator) Op. The operation command through the master arm 21 is transmitted to a master control unit 81 of a control unit 8, properly converted if necessary, and then input to a manipulator control unit 82. Subsequently, an actuation signal is transmitted from the manipulator control unit 82 to the slave manipulator 3, and thus the slave arm 31 is actuated.

As shown in FIG. 1, the slave manipulator 3 is installed at a surgical table 100 on which a patient P is placed. The slave arm 31 is configured to have a plurality of multi-degree-of-freedom joints and can be actuated in a multi-axial manner. Each of the multi-degree-of-freedom joints is individually driven by a power section (not shown). For example, a motor (servo motor) which has a servo mechanism equipped with an incremental encoder, a speed reducer, etc. may be used as the power section.

A treatment tool 50, which is inserted into a body of the patient P to perform a procedure, is attached to a distal end portion of the slave arm 31. The treatment tool 50 is inserted into a sheath 41 inserted into the body of the patient P and is introduced into the body via the sheath 41. Various types of treatment tools 50 in which a treatment portion of a distal end side has different structures and shapes are prepared to be used for different procedures, and various procedures are performed by replacing and mounting the treatment tools on the distal end portion of the slave arm 31. A configuration of the treatment tool 50 and a structure of a connection portion of the slave arm 31 will be described in detail later.

An observation means (not shown) such as an endoscope, which acquires an image of a procedure field including a procedure target portion to be operated on by the treatment tool 50, is introduced into the body of the patient P. A known device may be properly selected and used as the observation means. An introduction path of the observation means is not particularly limited. For example, the observation means may be attached to a dedicated slave arm and introduced, or a laparoscope may be used as the observation means and parenterally introduced by providing a port on an abdominal wall.

The master input section 2 includes a plurality of master arms 21 operated by the practitioner Op, and a display section 22 on which the image acquired by the observation means is displayed. Each of the master arms 21 has a known configuration actuated in a multi-axial manner, and includes a grip section 21A as an operation section which is gripped by the practitioner Op at the distal end side close to the practitioner Op so as to issue an operation command.

Figure 2:
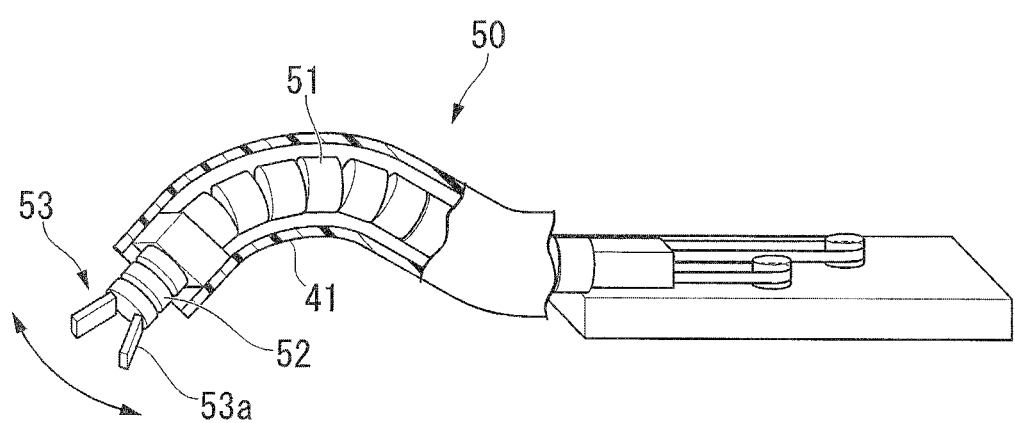
FIG. 2 is a schematic view illustrating a treatment tool of the master-slave system.

FIG. 2 is a schematic view illustrating a configuration of the treatment tool 50. The treatment tool 50 includes a long insertion section 51 having flexibility, a bending section 52 provided at a distal end side of the insertion section 51, and an end effector 53 attached to a tip of the bending section 52. The treatment tool 50 is configured as a so-called flexible treatment tool.

Figure 3:
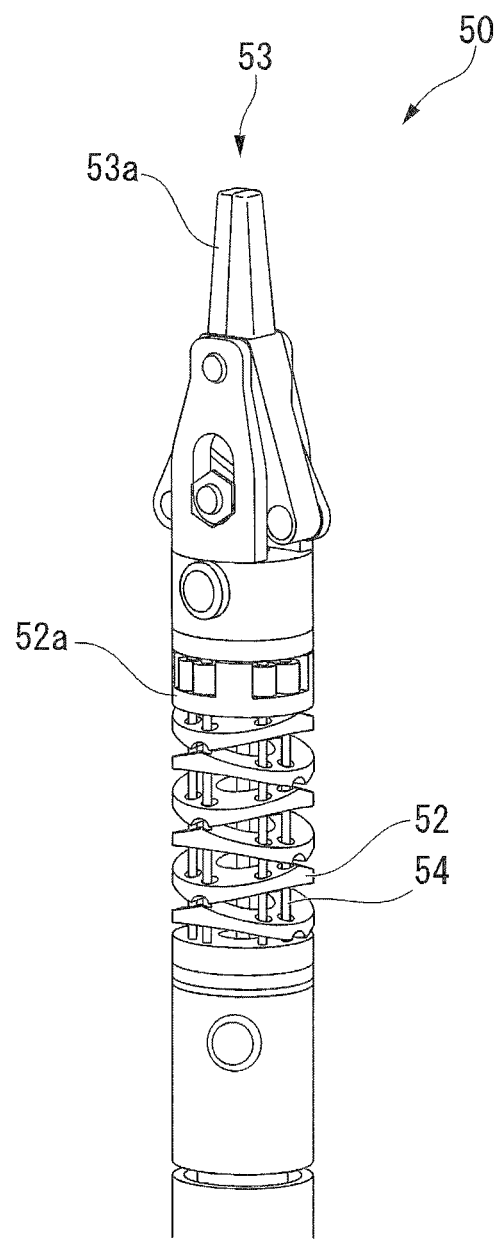
FIG. 3 is a partially enlarged view illustrating a distal end side of the treatment tool.

FIG. 3 is a partially enlarged view illustrating the distal end side of the treatment tool 50. The bending section 52 has a known configuration in which a plurality of joint rings 52a are arranged in an axial direction. Both end portions of an operation wire (operation member) 54 for driving the bending section 52 are fixed to the joint ring 52a located closest to the distal end, and the bending section 52 can be bent in two directions in a direction of a surface including the operation wire 54 by driving the operation wire 54.

In the embodiment, the end effector 53 serves as a gripping forceps including a pair of forceps pieces 53a. In the embodiment, the pair of forceps pieces 53a of the end effector 53 are opened and closed by advancing and retracting the operation member, such as the wire (not shown), attached to the forceps pieces 53a. However, since a basic structure of the forceps pieces 53a is known, a description thereof will be omitted here. In addition, a specific configuration of the end effector differs according to types of the treatment tool, and the operation member may also be excluded.

Figure 4:
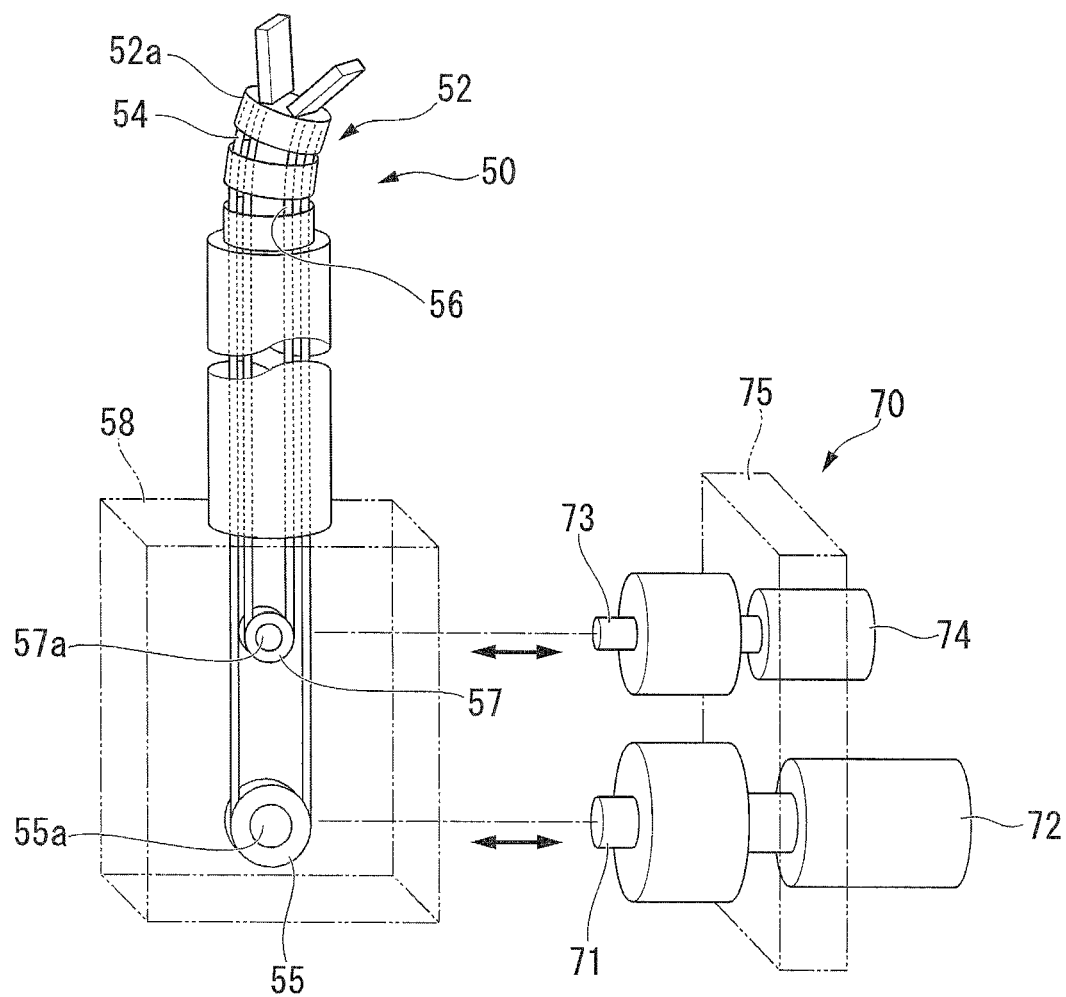
FIG. 4 is schematic view for explaining a structure for driving and curvature detection of the treatment tool.

FIG. 4 is schematic view for explaining a structure for driving and curvature detection of the treatment tool 50. An intermediate portion of the operation wire 54 is wound around a first pulley 55. The slave arm 31 is provided with a drive unit 70 for performing a bending operation of the treatment tool 50. When the treatment tool 50 is mounted to the slave arm 31, a first shaft (drive unit side drive shaft) 71 of the drive unit 70 engages with a shaft (treatment tool side drive shaft) 55a of the first pulley 55. A drive section 72 composed of a normal and reverse rotatable motor and the like is attached to the first shaft 71. When the drive section 72 is driven, the first shaft 71 is driven to rotate, driving thereof is transferred to the shaft 55a of the first pulley 55 so that the first pulley 55 is driven to rotate, and the operation wire 54 is driven.

A sensing wire (actuation amount detection member) 56 for detecting a bending direction and angular amount of the bending section 52 is attached to the bending section 52, independently of the operation wire 54. Similarly to the operation wire 54, both end portions of the sensing wire 56 are fixed to the joint ring 52a located closest to the distal end, and the sensing wire 56 is disposed on a proximal end side so as to be located on the same surface (including substantially the same surface) as the operation wire 54, so that the sensing wire 56 is wound around a second pulley 57. When the treatment tool 50 is mounted to the slave arm 31, a second shaft (drive unit side detection shaft) 73 of the drive unit 70 engages with a shaft (treatment tool side detection shaft) 57a of the second pulley 57. A detection section 74 composed of a rotary encoder and the like is attached to the second shaft 73. When the bending section 52 is bent, the sensing wire 56 is displaced according to curvature and the second pulley 57 rotates. The rotation of the second pulley 57 is transferred to the second shaft 73 and a displacement amount of the sensing wire 56 is detected by detecting a rotation direction and rotation amount of the second shaft 73 using the detection section 74.

Since operation force during the bending operation does not act on the sensing wire 56, the sensing wire 56 does not easily stretch in comparison to the operation wire 54 and can detect the displacement amount by suppressing generation of an error due to stretching.

As shown in FIG. 4, a base 58 for easy attachment and detachment to the slave arm 31 is attached to a proximal end side of the treatment tool 50. The shaft 55a of the pulley 55 and the shaft 57a of the pulley 57 are rotatably inserted into through-holes provided on the base 58. The drive unit 70 of the slave arm 31 is also provided with a base 75 having the same shape and size as the base 58. The first and second shafts 71 and 73 protrude from the base 75 through through-holes provided on the base 75. Since the shafts 55a and 57a in the base 58 are located at the same positions as the first and second shafts 71 and 73 in the base 75, a user can easily perform position adjustment between the shafts to be engaged by moving the base 58 such that the base 58 overlaps the base 75.

In addition, although not shown, the drive unit 70 has a shaft and a drive section for driving a wire opening and closing the end effector 53. As described above, when the treatment tool 50 is mounted, the pair of forceps pieces 53a of the end effector 53 can be opened and closed by the drive unit 70.

Figure 5:
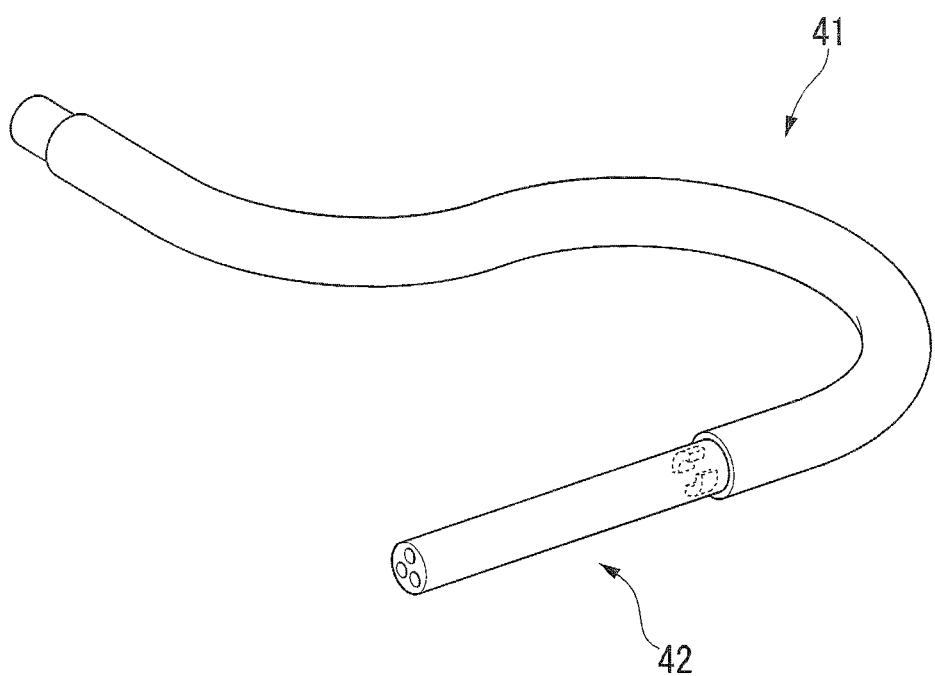
FIG. 5 is a perspective view illustrating a sheath of the master-slave system.

FIG. 5 is a perspective view illustrating the sheath 41. In the sheath 41, a proximal end side into which the treatment tool 50 is inserted is provided with a shape regulation section 42 used for phase setting (to be described later) of the shaft of the drive unit 70 when the treatment tool is replaced or remounted.

Figure 6B:
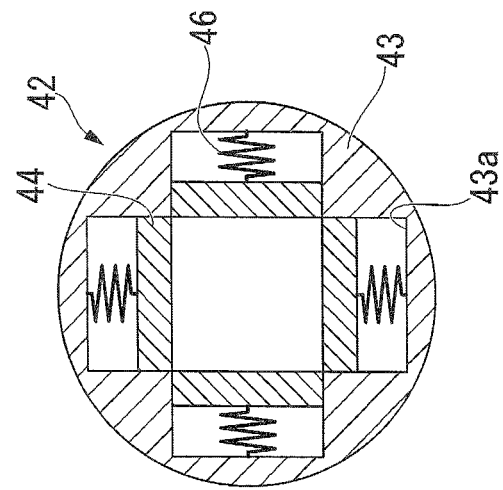
FIG. 6B is a radial cross-sectional view of the shape regulation section.
Figure 6A:
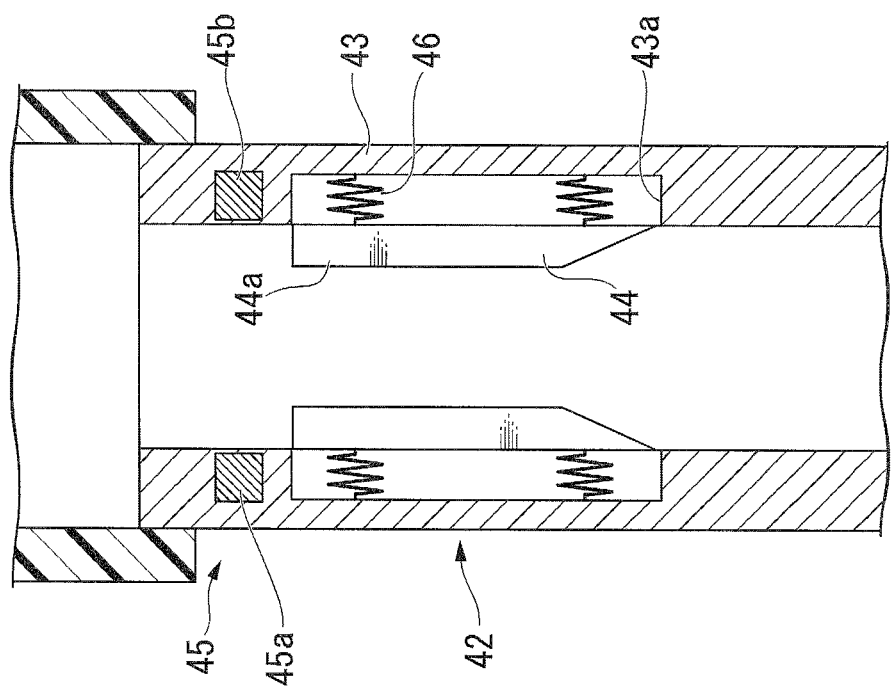
FIG. 6A is an axial cross-sectional view of a shape regulation section of the master-slave system.

FIG. 6A is an axial cross-sectional view of the shape regulation section 42. FIG. 6B is a radial cross-sectional view of the shape regulation section 42. The shape regulation section 42 includes a cylindrical body 43, four pressing members 44 which protrude from an inner surface of the body 43 to press the inserted treatment tool 50, and a detection unit 45 detecting that the bending section 52 of the inserted treatment tool 50 is accommodated in the shape regulation section 42.

Each of the pressing members 44 is a substantially rectangular parallelepiped member extending in an axial direction of the body 43 and has a pressing surface 44a parallel with the axis of the body 43. A concave section 43a having a size for allowing each pressing member 44 to enter is formed on an inner wall of the body 43. Each pressing member 44 is connected to an elastic member 46 attached to the concave section 43a. Accordingly, each pressing member 44 is urged so as to protrude from the inner wall to a lumen of the body 43 by the elastic member 46, and when the pressing member 44 is pressed radially outward from the body 43, the pressing member 44 compresses the elastic member 46 to enter the concave section 43a.

In a natural state with no external force, a distance between the pressing surfaces 44a of the facing pressing members 44 is set to be smaller than a diameter of the bending section 52 of the inserted treatment tool 50. In addition, a length of each pressing surface 44a in the axial direction of the body is set to be equal or greater than a length of the bending section 52.

In addition, a proximal end side of each pressing member 44 has an inclined surface shape for easy insertion of the treatment tool 50. As a result, a distance between the pressing members 44 arranged to face each other is gradually increased toward the proximal end side.

The detection unit 45 of the embodiment is a transmission sensor including a light emitting section 45a and a light receiving section 45b, and detects whether or not an object is present between the light emitting section 45a and the light receiving section 45b. The detection unit 45 is not particularly limited to a specific configuration and a detection principle as long as it is capable of detecting whether or not an object is present at a distal end side of the pressing member 44, and various known sensors may be used.

Figure 7:
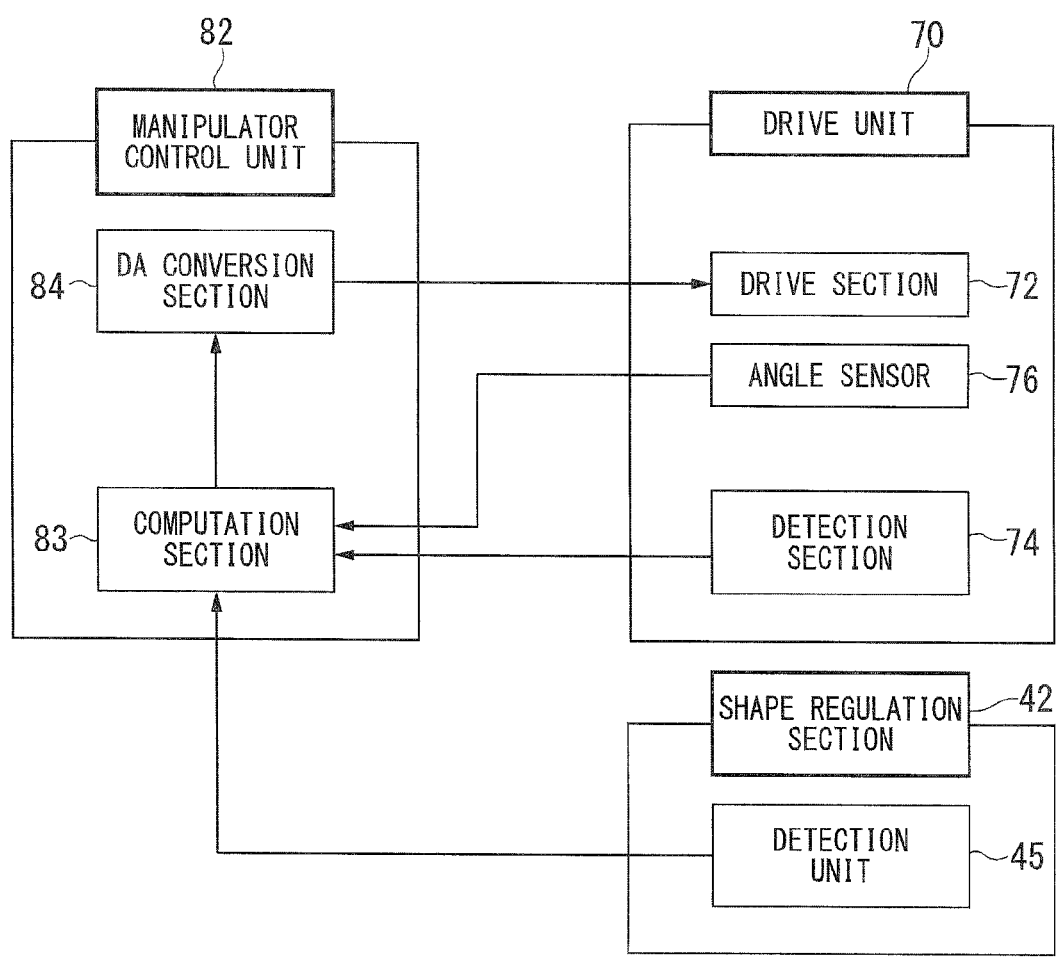
FIG. 7 is a functional block diagram illustrating a portion of a slave arm in the master-slave system.

FIG. 7 is a functional block diagram illustrating a portion of the slave arm 31. The manipulator control unit 82 includes a computation section 83 which calculates a driving amount of the drive section 72, and a DA conversion section 84 for generating a driving signal driving the drive section 72, based on the computed result of the computation section 83. The computation section 83 is connected to the detection section 74 of the drive unit 70 and an angle sensor 76 for detecting an angle of the drive section 72, and transmits these detection values of the mechanisms to the computation section 83. Furthermore, the detection unit 45 of the sheath 41 is also connected to the computation section 83. When the detection unit 45 detects an object, information thereof is transmitted to the computation section 83.

In addition, a connection mode of each section shown in FIG. 7 may be configured in a wired or wireless manner as long as signals can be transmitted and received and detection values can be interchanged.

The actuation during the use of the master-slave system 1 having the above-mentioned configurations will be described.

When the practitioner performs operation input to the master arm 21 for bending the bending section 52 of the treatment tool 50, the operation input is transmitted from the master control unit 81 to the manipulator control unit 82. The computation section 83 of the manipulator control unit 82 calculates a driving amount of the drive section 72, based on the received operation input. In the DA conversion section 84, the driving signal is generated based on the calculated driving amount and transmitted to the drive section 72 of the drive unit 70. When the drive section 72 is rotated in this way, the first pulley 55 of the treatment tool 50 is rotated so that the bending section 52 is bent in a desired direction by a desired angular amount.

When the treatment tool 50 is replaced, a user such as a practitioner or an assistant removes the base 58 of the treatment tool 50 from the drive unit 70 of the slave arm 31. Then, the user attaches the base of the replaced treatment tool to the base 75 of the drive unit 70. In this case, even if the first and second shafts 71 and 73 of the drive unit 70 are rotated after removal of the treatment tool, phases between the shafts 71 and 73 of the drive unit 70 and the shafts 55a and 57a of the treatment tool side can be properly adjusted by performing a predetermined actuation when a subsequent treatment tool is mounted. Consequently, the practitioner can properly operate the treatment tool without causing discomfort. It is described below in detail.

Figure 8:
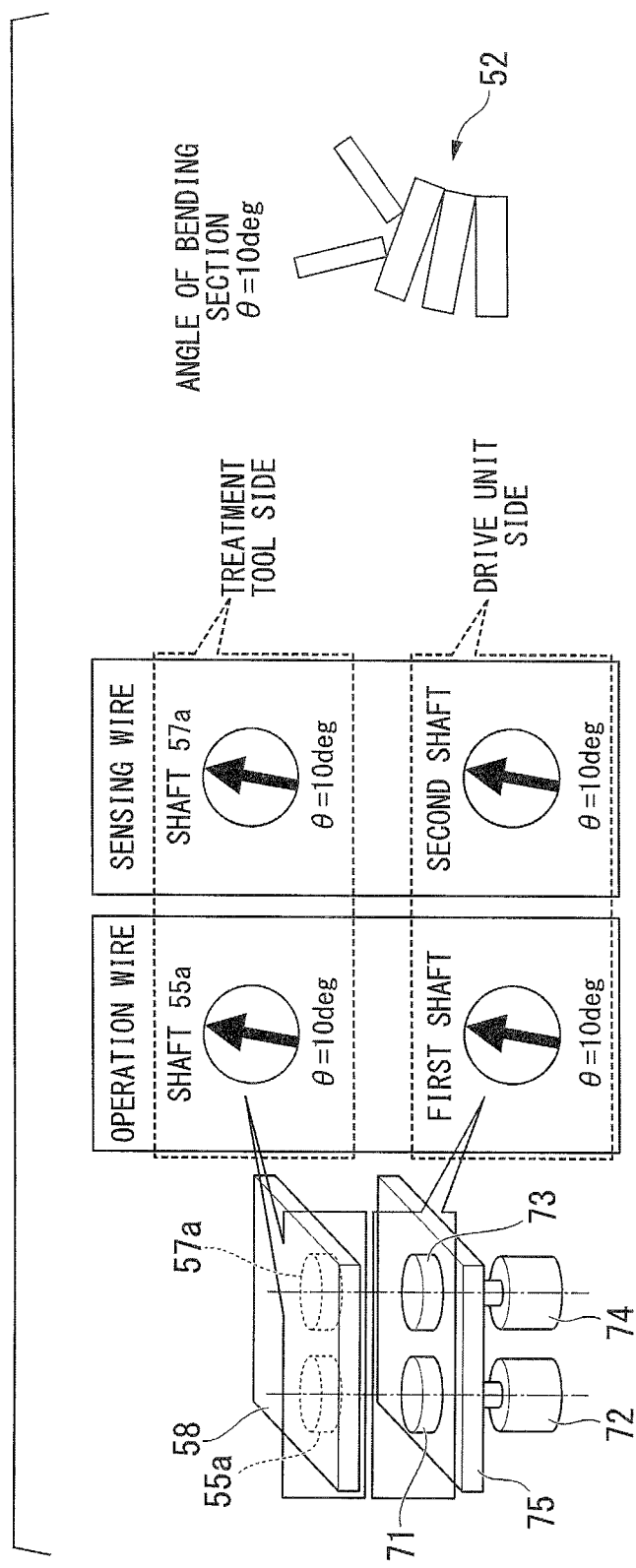
FIG. 8 is a view illustrating an example of phases of a treatment tool side shaft and a drive unit side shaft before replacement of the treatment tool.

First, before removal of the treatment tool 50, it is assumed that the phases between the shafts 71 and 73 of the drive unit 70 side and the shafts 55a and 57a of the treatment tool 50 side coincide. For example, when the bending section 52 is bent 10° to the right, all of the shafts 71 and 73 of the drive unit 70 side and the shafts 55a and 57a of the treatment tool 50 side indicate an angle of 10° inclined to the right as shown in FIG. 8. In addition, in the description after FIG. 8, a clockwise angle (up to 180°) is indicated by a positive value and a counterclockwise angle (up to 180°) is indicated by a negative value.

Figure 9:
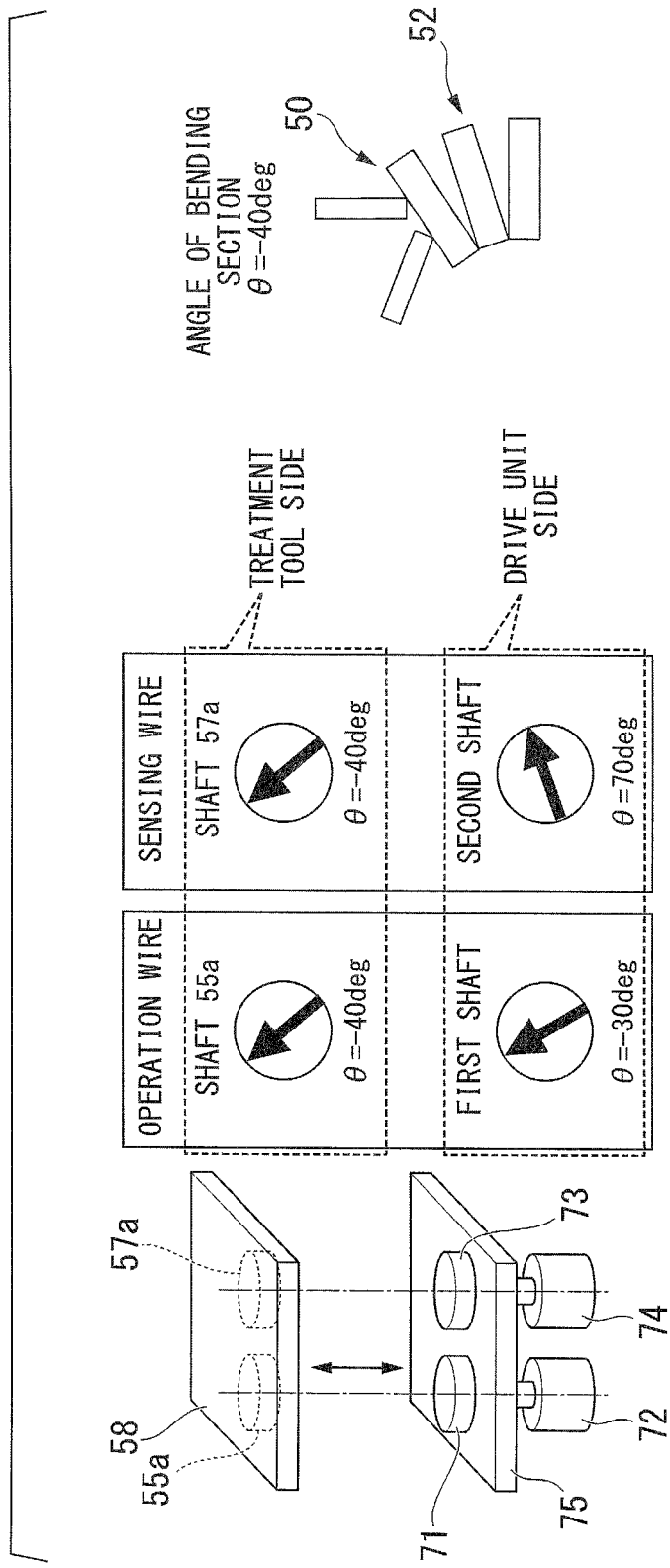
FIG. 9 is a view illustrating an example of phases of the treatment tool side shaft and the drive unit side shaft after removal of the treatment tool.

It is assumed that the treatment tool 50 is removed from the drive unit 70 in a state in which the bending section 52 is operated from the state shown in FIG. 8 and is bent 40° to the left. All of the shafts indicate an angle of −40° until just before removal of the treatment tool. In the treatment tool 50, since the operation wire 54 is wound in a state in which tension is applied to the operation wire 54, each of the shafts 55a and 57a is maintained in a state of indicating an angle of −40° as shown in FIG. 9 even after the treatment tool 50 is removed from the drive unit 70. On the other hand, since the first and second shafts 71 and 73 of the drive unit 70 are not restricted by the shafts 55a and 57a, respectively, unpredictable rotation of the first and second shafts 71 and 73 occurs due to external factors such as self-weight and the first and second shafts 71 and 73 indicate certain angles. For example, the first shaft 71 indicates an angle of −30° and the second shaft 73 indicates an angle of 70°, in FIG. 9.

Figure 10:
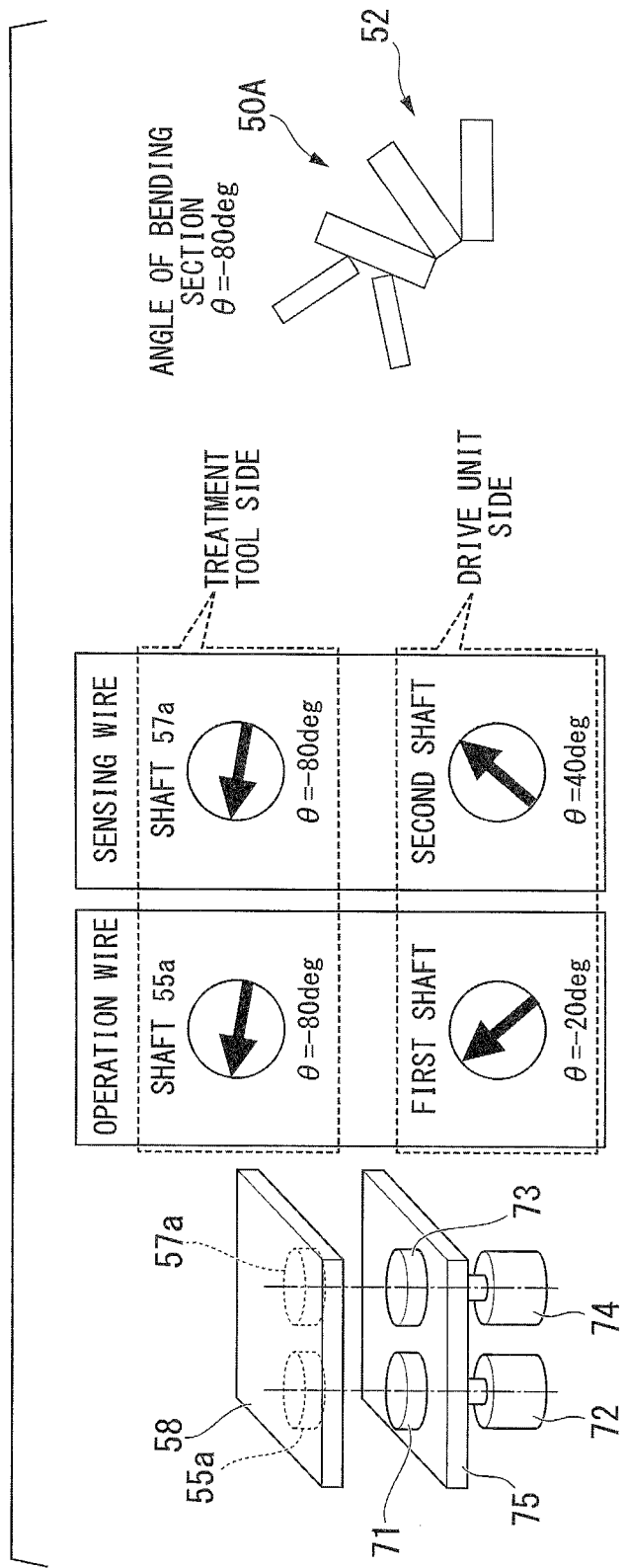
FIG. 10 is a view illustrating an example of phases of the treatment tool side shaft and the drive unit side shaft immediately after mounting of the treatment tool.
Figure 11:
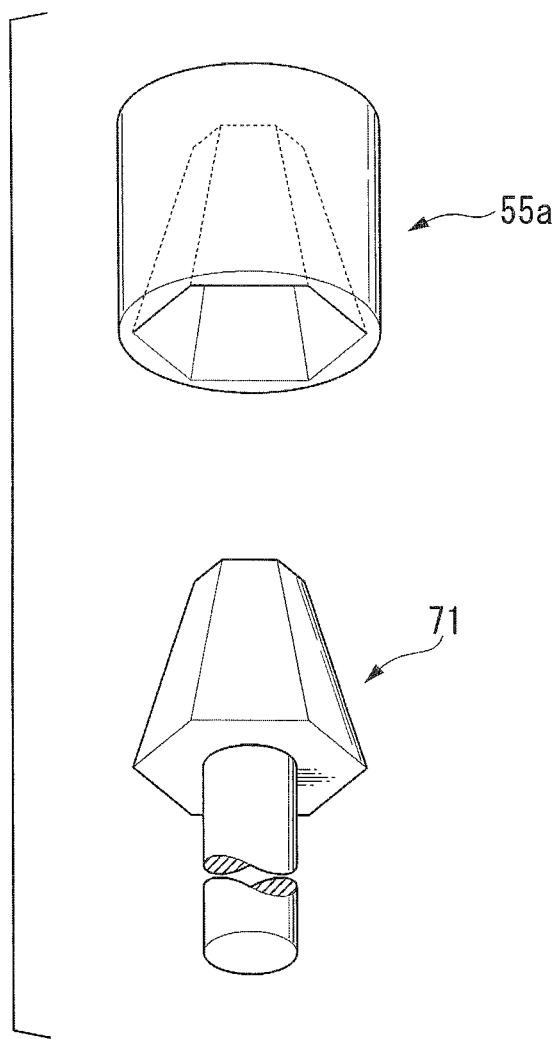
FIG. 11 is a view illustrating an example of shapes of the treatment tool side shaft and the drive unit side shaft.

Next, when a new treatment tool 50A is mounted to the drive unit 70, a direction and an angular amount of the bending section when the treatment tool 50A is mounted do not necessarily coincide with the state immediately before removal of the treatment tool 50. Accordingly, in FIG. 10, it is assumed that the bending section of the treatment tool 50A is bent 80° to the left. When the base 58 of the treatment tool 50A approaches the base 75 of the drive unit 70, the shaft 55a and the first shaft 71 engage with each other and the shaft 57a and the second shaft 73 engage with each other, and thus two of the shafts are engaged with each other. In this case, for example, as shown in FIG. 11, when a cross-section of an engagement portion between a shaft (for example, the shaft 55a) of the treatment tool side and a shaft (for example, the first shaft 71) of the drive unit side in a direction intersecting the axis has a regular hexagonal shape, the first and second shafts 71 and 73 rotating by smaller force properly rotate so as to engage with the shafts of the treatment tool side so that both engage with each other. As a result, for example, as shown in FIG. 10, the first shaft 71 engages with the shaft 55a in a state in which the first shaft 71 rotates 10° to the right to indicate an angle of −20°, and the second shaft 73 engages with the shaft 57a in a state in which the second shaft 73 rotates 30° to the left to indicate an angle of 40°. In FIG. 11, since the engagement portion has a hexagonal cross-sectional shape, a deviation amount of the first and second shafts 71 and 73 becomes an integral multiple of 60°, which is 360° divided by the number of angles of the cross-sectional shape.

Figure 12C:
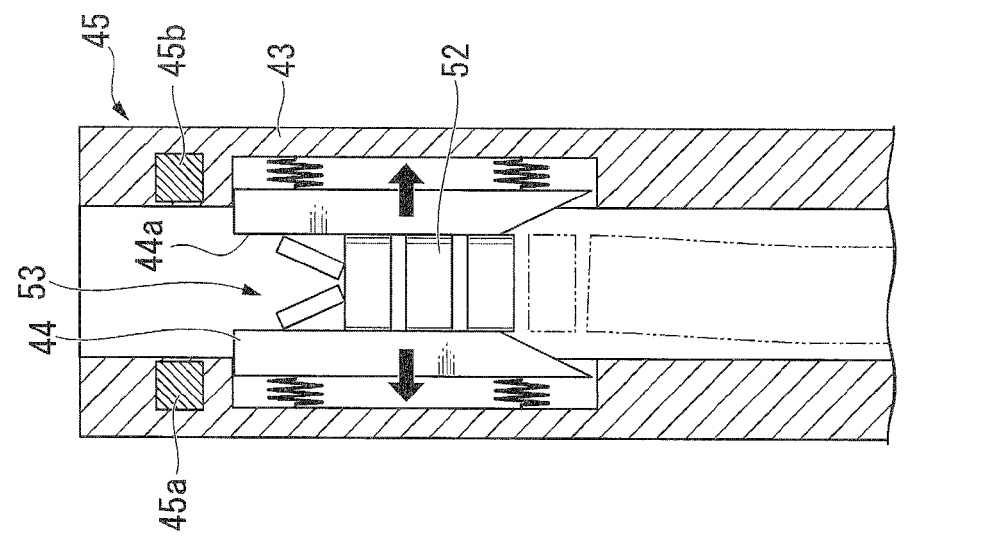
FIG. 12C is a view illustrating the shape regulation section and the treatment tool in one process during replacement of the treatment tool.
Figure 12B:
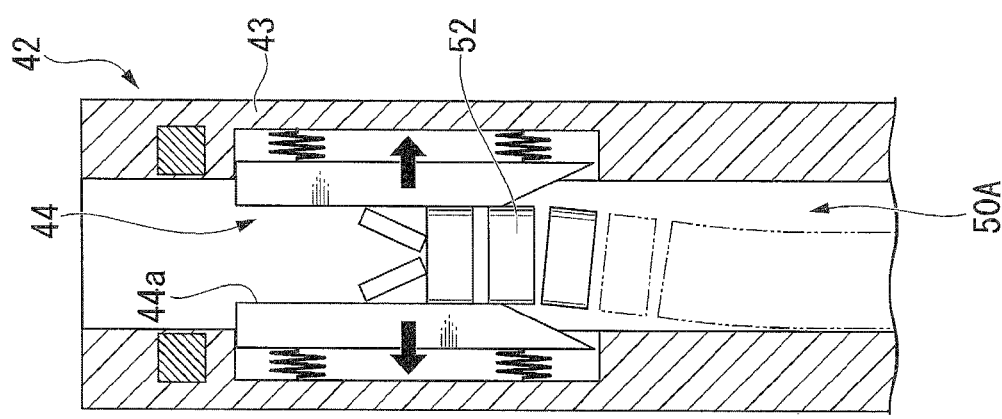
FIG. 12B is a view illustrating the shape regulation section and the treatment tool in one process during replacement of the treatment tool.
Figure 12A:
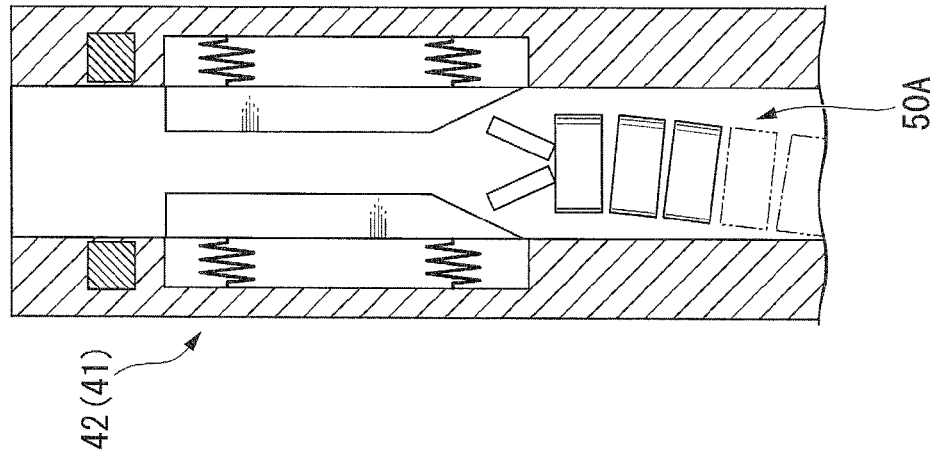
FIG. 12A is a view illustrating the shape regulation section and the treatment tool in one process during replacement of the treatment tool.

When the base 58 is mounted to the base 75 and the corresponding shafts engage with each other, the user inserts a distal end side of the treatment tool 50A into a proximal end side of the sheath 41. Thereby, as shown in FIG. 12A, the distal end side of the treatment tool 50A gradually enters the shape regulation section 42 of the sheath 41. The treatment tool 50A entering the shape regulation section 42 enters to the distal end side in the shape regulation section 42 while pressing the pressing members 44 toward the body 43, as shown in FIG. 12B. In the above process, the bending section 52 is pressed by the pressing surface 44a of each pressing member 44 to be deformed in a linear shape parallel with the axis of the body 43, as shown in FIG. 12C. Thereby, the shape of the bending section 52 is regulated and maintained in a state (a predetermined actuation state) in which a bending angle is 0° by the shape regulation section 42.

When the bending section 52 comes into contact with the pressing surface 44a in the axial direction, the end effector 53 moves between the light emitting section 45a and the light receiving section 45b, the end effector 53 is detected by the detection unit 45, and a detection signal is transmitted to the computation section 83. The computation section 83 receiving the detection signal sets rotation angles of the first and second shafts 71 and 73 at that point of time as a state in which the bending section 52 is 0° and matches the state with the shape of the bending section 52 regulated by the shape regulation section 42.

Figure 13:
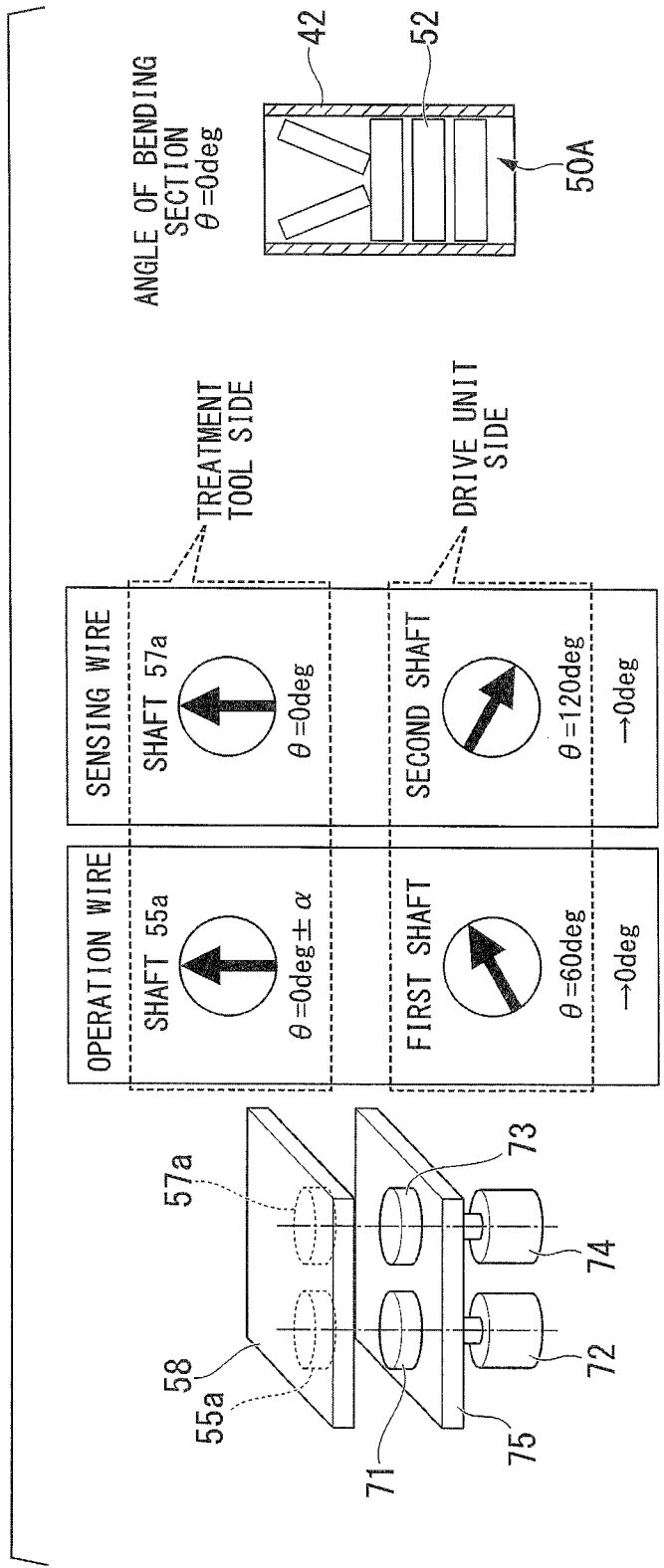
FIG. 13 is a view illustrating an example of phase adjustment of the treatment tool side shaft and the drive unit side shaft immediately after mounting of the treatment tool.

Such actuation will be described as an example shown in FIG. 10. Since the bending section 52 becomes a linear shape, namely, 0° after inserted into the shape regulation section 42 in a state of −80°, the shafts 55a and 57a of the treatment tool 50 rotate 80° to the right as shown in FIG. 13. Thus, the first and second shafts 71 and 73 respectively engaging with the shafts 55a and 57a rotate 80° to the right and respectively indicate angles of 60° and 120°. The computation section 83 sets the states as angles of 0° of the first and second shafts 71 and 73 and performs subsequent actuation control of the drive section 72 and detection of a displacement amount of the sensing wire 56 by the detection section 74 based on the position after the setting. Thereby, the phase adjustment between the shaft of the treatment tool side and the shaft of the drive unit side is completed.

In this case, a message, an image, or the like informing of completion of the phase adjustment associated with replacement of the treatment tool may be displayed on the display section 22, if necessary, such that the user may identify the same.

As described above, according to the master-slave system 1 of the embodiment, in a state in which the bending section 52 of the treatment tool 50A newly mounted to the drive unit 70 of the slave arm 31 when the treatment tool is replaced becomes a linear shape by the shape regulation section 42 of the sheath 41, the computation section 83 sets the rotation positions of the first and second shafts 71 and 73 of the drive unit 70 as 0° corresponding to the linear shape. Accordingly, since the phase adjustment between the shaft of the drive unit and the shaft of the treatment tool is performed without detecting the rotation positions of the first and second shafts 71 and 73, the drive unit can have a simple structure and complicated computation is not required in the computation section.

In addition, since the detection unit 45 is provided in the shape regulation section 42, the phase adjustment between the drive unit and the treatment tool is automatically performed only by inserting the insertion section 51 of the new treatment tool into the sheath 41 when the user replaces the treatment tool. Accordingly, the phase adjustment can be performed without additional operation by the user and the procedure can be smoothly performed.

Furthermore, since the proximal end side of the pressing member 44 has an inclined surface shape, the insertion section of the inserted treatment tool is difficult to be caught and can be smoothly inserted.

Second Embodiment

Figure 15:
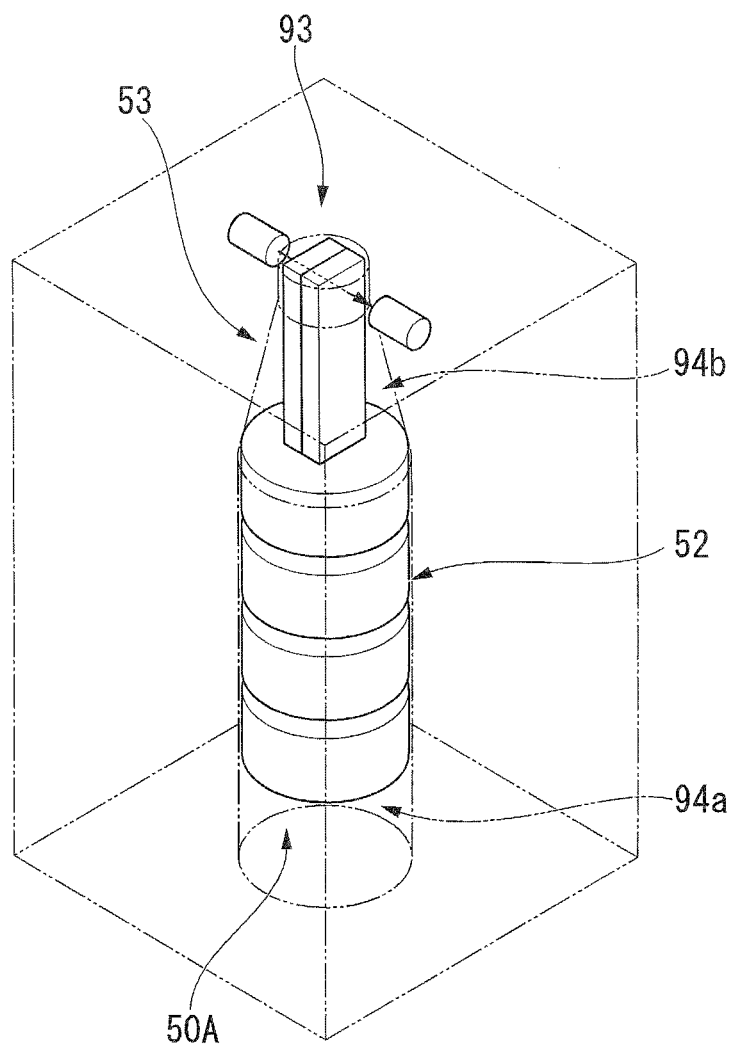
FIG. 15 is a view illustrating a state in which a treatment tool is inserted into the shape regulation section.
Figure 16:
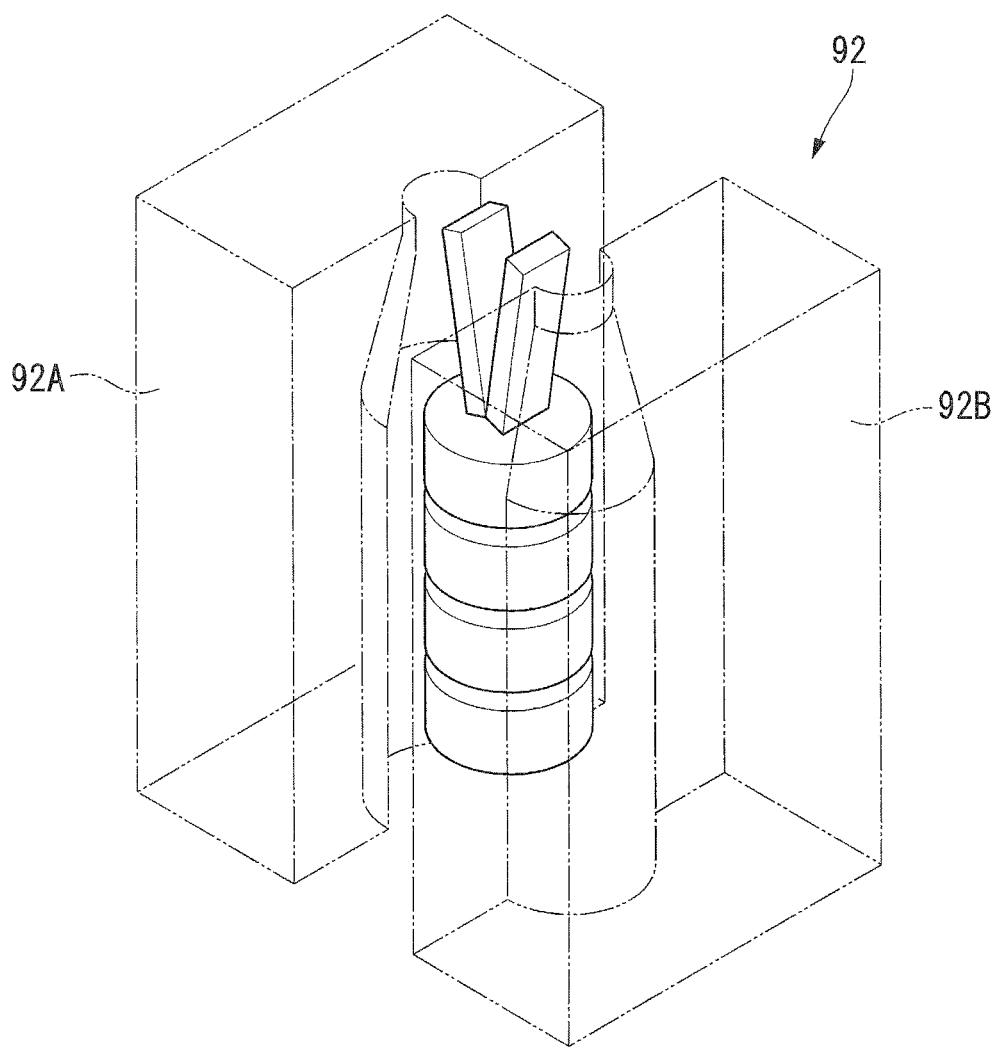
FIG. 16 is a view illustrating a modified example of the shape regulation section.

Next, a second embodiment of the present invention will be described with reference to FIGS. 14 to 16. The present embodiment differs from the first embodiment in that the shape regulation section is provided in a manner separated from the sheath. The same elements as in the above-mentioned embodiment are designated by like reference numerals and a redundant description thereof will be omitted here.

Figure 14:
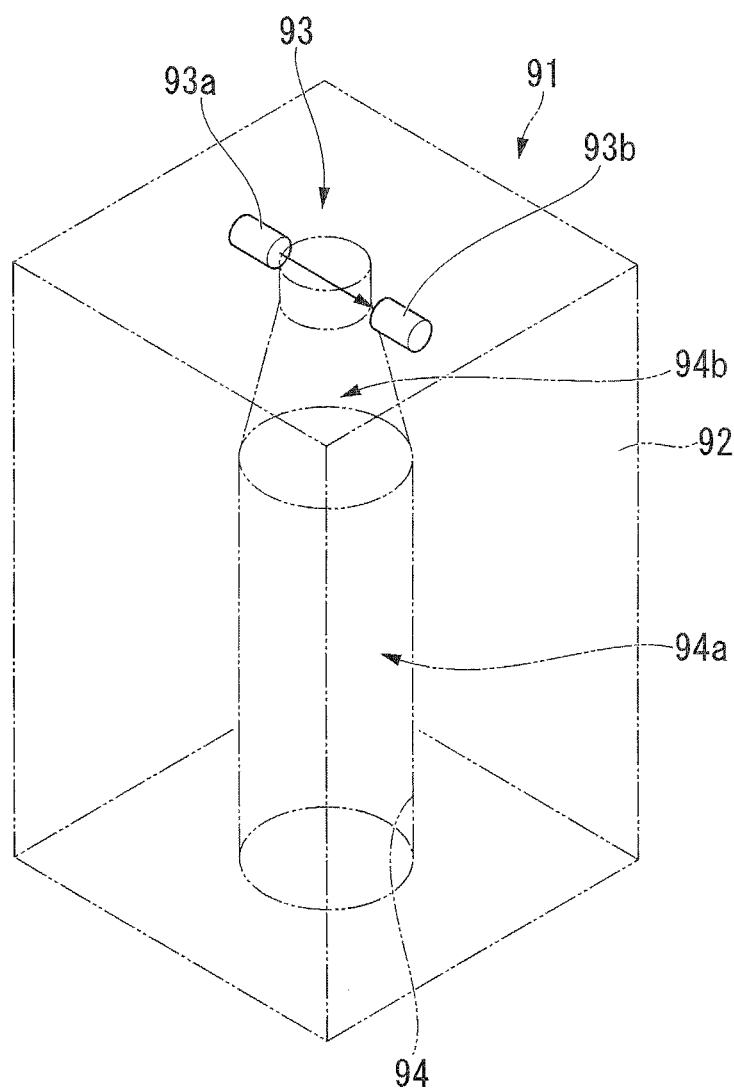
FIG. 14 is a view illustrating a shape regulation section in a master-slave system according to a second embodiment of the present invention.

FIG. 14 is a view illustrating a shape regulation section 91 in a master-slave system according to the present embodiment. The shape regulation section 91 is not present in a portion of the sheath and is configured as an independent jig. The shape regulation section 91 includes a body 92 and a detection unit 93.

The body 92 is formed with a hole portion 94 for regulating the bending section 52 in a linear shape by insertion of the bending section 52. The hole portion 94 includes a first region 94a extending in a linear shape by an inner diameter having a slightly greater than an outer diameter of the bending section 52 and a second region 94b extending while having a reduced diameter than the first region 94a in a depth direction. The dimension in the axial direction of the first region 94a is equal to or greater than the dimension in the axial direction of the bending section 52, and the dimension in the axial direction of the second region 94b is substantially equal to the dimension in the axial direction of the end effector 53 in a state in which the end effector 53 is closed. Similarly to the detection unit 45 of the first embodiment, the detection unit 93 has a light emitting section 93a and a light receiving section 93b and is disposed at the deepest side of the second region 94b. The detection unit 93 is connected to the computation section 83 so as to transmit signals to the computation section 83. A connection mode may be configured in a wired or wireless manner.

The actuation during replacement of the treatment tool in the master-slave system of the embodiment will be described.

After a new treatment tool 50A is mounted to the drive unit 70 by the same operation as the first embodiment, the user inserts a distal end side of the treatment tool 50A into the hole portion 94 of the shape regulation section 91. In addition, in the embodiment, a shaft of a pulley around which the operation member for opening and closing the end effector 53 is wound is disposed at the base 58, a shaft for driving the pulley is provided at the base 75, and the two shafts also engage with each other when the treatment tool 50A is mounted.

The bending section 52 is regulated in a linear shape by the bending section 52 entering the first region 94a of the hole portion 94. In this case, the end effector 53 enters the second region 94b and comes into contact with an inner wall of the second region 94b having a gradually reduced diameter so as to be closed. As shown in FIG. 15, when the bending section 52 is fully accommodated in the first region 94a, the end effector 53 is also regulated in a closed shape. When the distal end portion of the closed end effector 53 is detected by the detection unit 93, similarly to the first embodiment, positions of the first shaft, the second shaft, and the shaft for driving the above end effector 53 at point of time at which the distal end portion is detected are set as 0° by the computation section 83 and phase adjustment is performed.

Similarly to the first embodiment, in the present embodiment, the phase adjustment between the treatment tool and the drive unit can be simply performed with no need for complicated structure and computation.

In addition, since the second region 94b is provided in the hole portion of the shape regulation section 91, the end effector can also be regulated in a predetermined shape, in addition to the bending section. As a result, the phase adjustment can be simply performed with respect to the drive shaft of the end effector.

Furthermore, since the shape regulation section 91 is provided independently of the sheath, the typical disposable sheath may have a simple structure and manufacturing costs may be suppressed.

In the embodiment, the body of the shape regulation section may not necessarily be integrated. For example, as shown in a modified example of FIG. 16, a body 92 is configured by two members which are members 92A and 92B having grooves, and a hole portion 94 may be formed when the members 92A and 92B are combined. By such a configuration, the treatment tool is disposed along the groove of one member and then the other member is adjusted, thereby enabling the bending section 52 and the end effector 53 to be regulated in a desired shape. Therefore, accommodation operation to the hole portion 94 of the bending section is simple and easy.

Although embodiments of the present invention have been described, the scope of the present invention is not limited to the embodiments. Variations in combination of constituent elements, modifications to the constituent elements, deletions of the constituent elements, and other variations may be made to the present invention without departing from the scope of the present invention.

For example, although an example in which treatment tool has a set of the operation member and the shaft actuating the operation member and be bent by one shaft has been described in each embodiment, the treatment tool of the present invention is not limited thereto. Of course, the treatment tool may also be bent by two shafts. In this case, the operation member and the sensing wire in the second shaft may be disposed at the base of the treatment tool and the shaft of the drive section and the shaft of the detection section corresponding to the same may be similarly disposed at the base of the drive unit. Further, in addition to the state in which the above bending section and end effector are opened, the rotation position of the insertion section of the end effector about the axis thereof may be regulated by the shape regulation section. Such a modified example will be described below.

Modified Example

Figure 17:
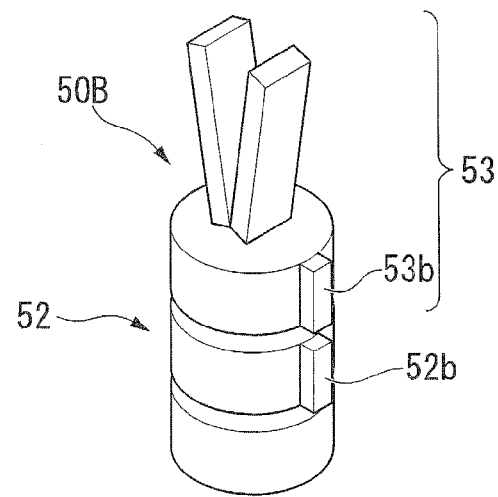
FIG. 17 is a schematic view illustrating a distal end portion of a treatment tool in a modified example of the present invention.
Figure 18:
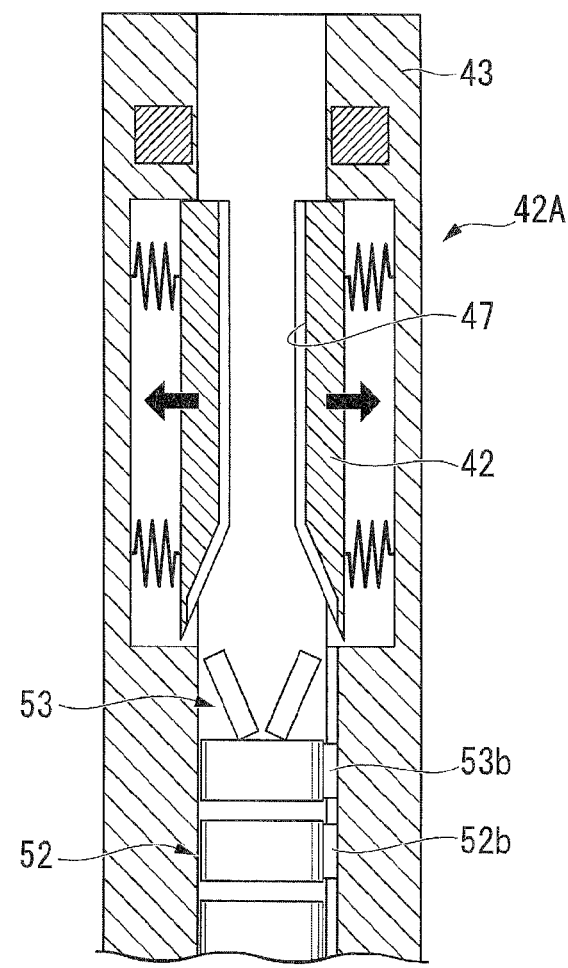
FIG. 18 is a view illustrating a state in which the treatment tool is inserted into the shape regulation section in the modified example.

A treatment tool 50B of a modified example shown in FIG. 17 is provided with a protrusion 53b protruding radially outwardly than an outer surface of the bending section 52 in the end effector 53. A portion of the bending section 52 is also provided with a protrusion 52b protruding in the same form as the protrusion 53b. As shown in FIG. 18, in a shape regulation section 42A of the modified example, grooves 47 which the protrusions 52b and 53b can enter are formed on a body 43 and a pressing member 44. Accordingly, the treatment tool 50B cannot be inserted into the shape regulation section 42A unless phases between the protrusions 52b and 53b coincide. The bending section 52 is regulated in a linear shape and at the same time the rotation position of the end effector 53 is also regulated in a determined state by mating the phase of the protrusion 52b with the phase of the protrusion 53b and inserting the protrusions 52b and 53b into the shape regulation section 42A by the user. The regulation of the rotation position by the grooves and the protrusions may also be applied to a jig type shape regulation section in the second embodiment.

Figure 19A:
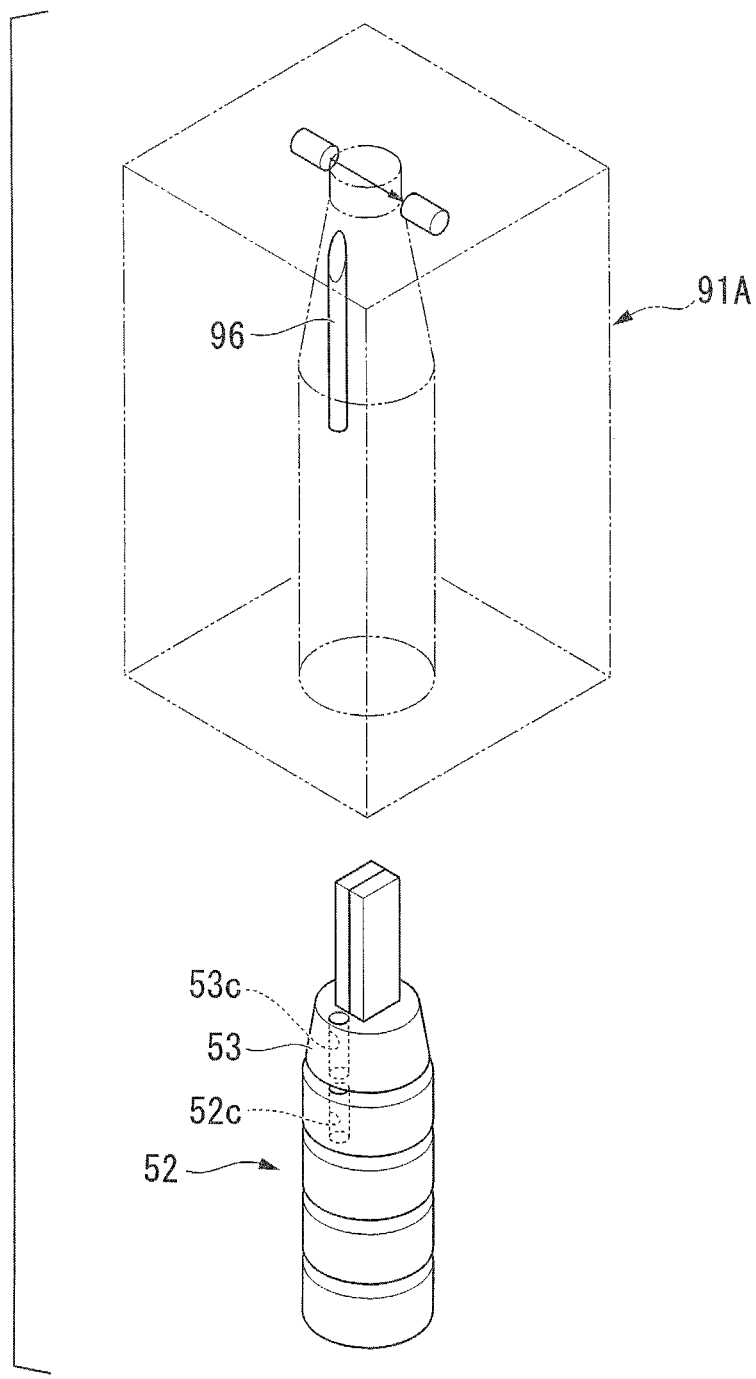
FIG. 19A is a view illustrating a shape regulation section and a treatment tool in another modified example of the present invention.
Figure 19B:
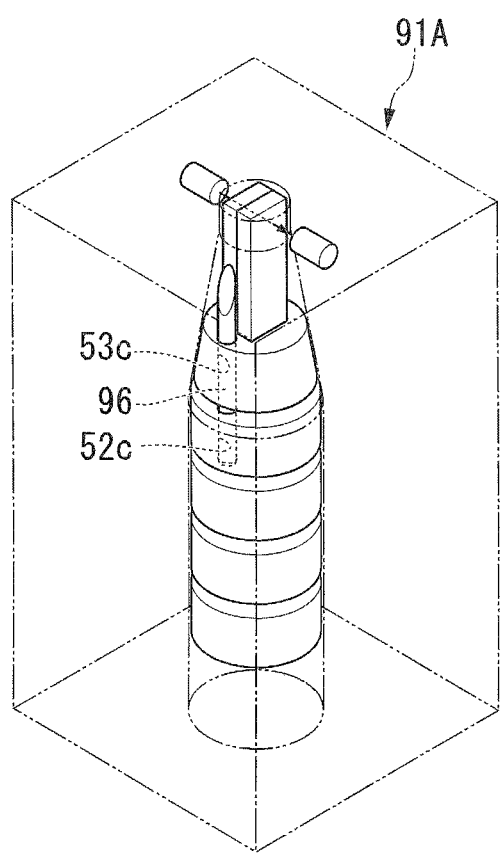
FIG. 19B is a view illustrating a state in which the treatment tool is inserted into the shape regulation section.

A structure in which the positional relation between the end effector and the bending section is regulated in a predetermined state is not limited to the above groove and protrusion. For example, as shown in FIG. 19A, by using a shape regulation section 91A having a pin 96 extending in parallel with a lumen, the end effector 53 and the bending section 52 are respectively provided with insertion sections 53c and 52c into which the pin 96 can be inserted. By such a configuration, when the end effector 53 and the bending section 52 are inserted into the shape regulation section 91A, as shown in FIG. 19B, phases between the insertion sections 53c and 52c should coincide and phases between the two insertion sections 53c and 52c and the pin 96 should coincide. Therefore, the positional relation between the end effector 53 and the bending section 52 can be regulated in a predetermined state only by inserting the end effector 53 and the bending section 52 into the shape regulation section 91A.

In addition, even if the end effector is not rotated with respect to the bending section, the end effector protruding from the sheath can be in a predetermined state by regulating the rotation position of the treatment tool with respect to the sheath in a predetermined phase. Accordingly, in the shape regulation section provided integrally with the sheath, the configuration of the above modified example may also be adopted. In this case, the protrusions and the insertion sections may also be provided at any portions not rotating with respect to the end effector with no need for provision at both of the end effector and the bending section. In this case, the rotation position of the treatment tool with respect to the sheath may be regulated in a predetermined phase by a spiral groove provided in the shape regulation section and a protrusion engaging with the spiral groove.

In addition, if the shape regulation section is provided independently of the sheath, the treatment tool may be inserted into the shape regulation section in a state in which the relative positional relation between the sheath and the shape regulation section in the rotation direction is fixed. In this case, the relative positional relation between the sheath and the shape regulation section may also be fixed through a reference plane such as a floor or the above base.

In addition, although an example of the master-slave manipulator in which the remote operation is performed by the master input section is described in each embodiment, the medical manipulator of the present invention is not limited thereto. For example, a portion in which the operation input is performed may be integrated with the drive unit in the medical manipulator.

Furthermore, the bending section regulated by the shape regulation section is not limited to be a linear shape. For example, the bending section may also be configured so as to be regulated in a state in which the bending section is bent in a desired direction by a desired angle. In this case, the computation section sets the direction and angle of the shaft of the drive unit in the state in which the bending section is bent in the desired direction by the desired angle to be equal to the direction and angle of the bending section, thereby enabling the same effect to be obtained.

In addition, in the shape regulation section of the present invention, the detection unit is not necessarily required. For example, the shape regulation section is formed as a transparent member and when the user has identified that the bending section is reliably regulated in a predetermined actuation state by the shape regulation section, a predetermined operation input is performed to interface of the operation section or the display section. When the computation section receives signals by the operation input, the phase adjustment may also be performed by updating the setting of the shaft of the drive unit. In this case, the user may regulate the treatment tool in a predetermined actuation state and then mount the treatment tool to the drive unit.

Furthermore, the concave/convex configuration for shaft engagement and the concave/convex relation such as the protrusion and the slit illustrated in each embodiment may also be reversed. In addition, since the deviation amount of the shaft of the drive unit is not used in the phase adjustment in the present invention, the engagement portion does not necessarily have a regular polygonal cross-section and the specific shape of the engagement portion may be properly designed in terms of driving force transfer efficiency or the like.

In addition, the medical manipulator of the present invention may also include various types of shape regulation sections having predetermined actuation states which are differently regulated. In this case, setting phase information for each shape regulation section may be stored in a phase setting section and the phase may also be set as a predetermined value according to identification information of the used shape regulation section.

In addition, in the treatment tool replacement method of the present invention, the user may also maintain the shape of the treatment tool in a predetermined actuation state and then perform the phase setting by inputting phase information corresponding to the predetermined actuation state.

In addition, the shape of the treatment tool may be maintained in a predetermined actuation state and then the treatment tool may be mounted to the drive unit.

The present invention is not to be considered as being limited by the foregoing description, and is only limited by the scope of the appended claims.

What is claimed is:

1. A treatment tool replacement method in a medical manipulator, the method comprising:
   providing the medical manipulator, the medical manipulator including a drive unit; a treatment tool detachably mounted on the drive unit and configured to be driven by the drive unit; an operation member connected to the treatment tool and configured to operate the treatment tool; a treatment tool side drive shaft configured to rotate so as to drive the operation member; an operation amount detection member connected to the treatment tool; a treatment tool side detection shaft configured to rotate in accordance with displacement of the operation amount detection member; a drive unit side drive shaft having a drive actuator configured to generate a driving force, the drive unit side drive shaft being installed at the drive unit, the drive unit side drive shaft being configured to be engaged with the treatment tool side drive shaft so as to transmit the driving force to the treatment tool side drive shaft; and a drive unit side detection shaft having a detection sensor configured to detect a displacement amount of the operation amount detection member, the drive unit side detection shaft being installed at the drive unit, the drive unit side detection shaft being configured to be engaged with the treatment tool side detection shaft such that rotation of the treatment tool side detection shaft is transmitted to the drive unit side detection shaft;
   mounting the treatment tool on the drive unit, and engaging the treatment tool side drive shaft with the drive unit side drive shaft and engaging the treatment tool side detection shaft with the drive unit side detection shaft;
   holding a shape of the treatment tool to a predetermined shape in which the treatment tool is operated by a predetermined operation amount; and
   setting phases in rotational directions of the treatment tool side drive shaft and the treatment tool side detection shaft to correspond to the predetermined operation shape.

2. A medical manipulator including:
   a drive unit
   a treatment tool detachably mounted on the drive unit and configured to be driven by the drive unit;
   an operation member connected to the treatment tool and configured to operate the treatment tool;
   a treatment tool side drive shaft configured to rotate so as to drive the operation member;
   an operation amount detection member connected to the treatment tool;
   a treatment tool side detection shaft configured to rotate in accordance with displacement of the operation amount detection member;
   a drive unit side drive shaft having a drive actuator configured to generate a driving force, the drive unit side drive shaft being installed at the drive unit, the drive unit side drive shaft being configured to be engaged with the treatment tool side drive shaft so as to transmit the driving force to the treatment tool side drive shaft;
   a drive unit side detection shaft having a detection sensor configured to detect a displacement amount of the operation amount detection member, the drive unit side detection shaft being installed at the drive unit, the drive unit side detection shaft being configured to be engaged with the treatment tool side detection shaft such that rotation of the treatment tool side detection shaft is transmitted to the drive unit side detection shaft;
   a shape regulation section regulating a shape of the treatment tool to a predetermined shape; and
   a controller configured to set phases in rotational directions of the treatment tool side drive shaft and the treatment tool side detection shaft,
   wherein the controller sets the phases of the treatment tool side drive shaft and the treatment tool side detection shaft to correspond to the predetermined shape when the controller receives a predetermined signal.

3. The medical manipulator according to claim 2, wherein the shape regulation section has a shape regulation sensor configured to send a signal to the controller when the treatment tool is regulated as the predetermined shape, and the controller sets the phases of the treatment tool side drive shaft and the treatment tool side detection shaft to correspond to the predetermined shape when the controller receives the signal from the shape regulation sensor.

4. The medical manipulator according to claim 3, wherein the shape regulation sensor is an optical sensor.

5. The medical manipulator according to claim 2, wherein the treatment tool has a bending section, and the predetermined shape is a shape in which the bending section is linear.

6. The medical manipulator according to claim 5, wherein the treatment tool further has an end effector installed at a tip of the bending section, and the shape regulation section has a first region configured to regulate a shape of the bending section and a second region configured to regulate a shape of the end effector.

7. The medical manipulator according to claim 5, wherein the shape regulation section has a pressing member configured to press the bending section to become a linear shape.

8. The medical manipulator according to claim 2, wherein the drive actuator is a motor.

9. The medical manipulator according to claim 2, wherein the detection sensor is a rotary encoder.

\* \* \* \* \*